(12) United States Patent
Scott et al.

(10) Patent No.: US 8,557,294 B2
(45) Date of Patent: *Oct. 15, 2013

(54) FILM COATING FOR TABLETS AND CAPLETS

(75) Inventors: Robert Anthony Scott, Sint-Niklaas (BE); Dominique Cade, Colmar (FR); Frederic Hoehn, Eschentzwiller (FR); Ewart Thomas Cole, Hofstetten (CH)

(73) Assignee: Capsugel Belgium NV, Bornem (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/034,928

(22) Filed: Feb. 25, 2011

(65) Prior Publication Data

US 2011/0142925 A1     Jun. 16, 2011

Related U.S. Application Data

(63) Continuation of application No. 10/637,484, filed on Aug. 8, 2003, now Pat. No. 7,914,820.

(30) Foreign Application Priority Data

Aug. 9, 2002    (EP) .................................... 02292020

(51) Int. Cl.
    *A61K 9/14*    (2006.01)
(52) U.S. Cl.
    USPC ............ 424/489; 424/490; 514/962; 514/963
(58) Field of Classification Search
    None
    See application file for complete search history.

(56) References Cited

U.S. PATENT DOCUMENTS

| | | | |
|---|---|---|---|
| 5,026,560 A | 6/1991 | Makino et al. | 424/494 |
| 5,344,825 A | 9/1994 | Khanna et al. | 514/108 |
| 5,630,871 A | 5/1997 | Jordan | 106/162.7 |
| 6,165,513 A | 12/2000 | Dansereau et al. | 424/490 |
| 6,245,350 B1 | 6/2001 | Amey et al. | 424/456 |
| 2002/0098227 A1* | 7/2002 | Nouri et al. | 424/439 |
| 2002/0098232 A1 | 7/2002 | Midha et al. | 424/457 |

FOREIGN PATENT DOCUMENTS

| | | |
|---|---|---|
| DE | 10033023 | 1/2002 |
| EP | 0551700 | 7/1993 |
| EP | 0930068 | 7/1999 |
| EP | 0891180 | 7/2002 |
| FR | 2288514 | 5/1976 |
| JP | 5144624 | 6/1993 |
| JP | 6157325 | 6/1994 |
| JP | 11139960 | 5/1999 |
| WO | WO 9737629 | 10/1997 |
| WO | WO 0045794 | 8/2000 |
| WO | WO 0203967 | 1/2002 |

OTHER PUBLICATIONS

Al-Dujalil, H., et al., "In-vitro Assessment of the Adhesiveness of Film Coated Tablets", International Journal of Pharmaceuticals (Amsterdam), 1986, pp. 67-74, 34(1-2).
WO0203967 is an English equivalent of German patent DE10033023, Jan. 17, 2002.

* cited by examiner

*Primary Examiner* — James Rogers
(74) *Attorney, Agent, or Firm* — Finnegan, Henderson, Farabow, Garrett & Dunner LLP

(57) ABSTRACT

The present invention relates to novel coating compositions for application to solid dosage forms such as tablets or caplets, solid dosage forms coated with the composition, and methods of preparing said coating compositions.

4 Claims, No Drawings

FILM COATING FOR TABLETS AND CAPLETS

This application is a continuation application of U.S. patent application Ser. No. 10/637,484, filed on Aug. 8, 2003, which claims priority to European Patent Application No. 02292020.1, filed on Aug. 9, 2002, the disclosures of which are hereby incorporated by reference in their entireties.

The present invention relates to novel coating compositions for application to solid dosage forms such as tablets or caplets, solid dosage forms coated with the composition, and methods of preparing said coating compositions.

EP-A-0 891 180 describes a process for encapsulation of caplets in a capsule wherein caplets are encapsulated in capsule shells. To obtain tamper-proof solid dosage forms, the caplets which are to be included into capsule shells, are coated with an acceptable coating for caplet processing. As described in EP-A-0 891 180 said coating is selected from a material selected from the group consisting of cellacephate, polyvinyl acetate phthalate, methacrylic acid polymers, hypromellose phthalate, hydroxyalkyl methyl cellulose phthalates or mixtures thereof.

After being coated with such a coating the caplet is usually feeded on a vibratory feed, filled into capsule shell parts and the encapsulated dosage form is dried so as to obtain capsules.

In several studies carried out by the present invention on finished capsules prepared as mentioned above, it has, however, been found that after obtaining said capsules the shell parts can be removed so as to lay free intact shell parts and caplets.

This should be prohibited so as to avoid any exchange of the caplets contained in said capsules by non-authorized persons after putting said capsules on the market.

Object of the present invention therefore is to provide coating compositions which give raise to capsules in a tamper-proof form which cannot be easily freed from the shell parts without deteriorating the shell parts and/or the caplets.

It is another object of the present invention to provide a coating composition which improves a feeding of solid dosage forms such as caplets or tablets, coated with said coating composition, on a vibratory feed used for example in a capsule manufacturing process.

It is yet another object of the present invention to provide a method for coating solid dosage form such as caplets or tablets with said coating composition.

It is yet another object of the present invention to provide a method for encapsulating caplets in a capsule in a tamper-proof form.

According to a first aspect, the present invention provides a coating composition comprising a film forming agent in an amount of from 0 to about 85% by weight, an adhesion enhancing agent in an amount of from about 10 to about 90% by weight, and a glidant in an amount of from about 5 to about 50% by weight, based on the weight of the coating composition.

According to a second aspect the present invention provides a solid dosage form coated with a coating composition comprising a film forming agent in an amount of from 0 to about 85% by weight, an adhesion enhancing agent in an amount of tram about 10 to about 90% by weight, and a glidant in an amount of from about 5 to about 50% by weight, based on the weight of the coating composition.

According to a third aspect, the present invention provides a method of preparing a coating composition comprising bringing into association a film forming agent in an amount of from 0 to about 85% by weight, an adhesion enhancing agent in an amount of from about 10 to about 90% by weight, and a glidant in an amount of from about 5 to about 50% by weight, based on the weight of the coating composition.

According to a forth aspect, the present invention provides a method of preparing a solid dosage form which comprises coating a solid dosage form core with a coating composition comprising a film forming agent in an amount of from 0 to about 85% by weight, an adhesion enhancing agent in an amount of from about 10 to about 90% by weight, and a glidant in an amount of from about 5 to about 50% by weight, based on the weight of the coating composition.

In a preferred embodiment of the first aspect said coating composition comprises a film forming agent in an amount of from about 0 to about 40% by weight, an adhesion enhancing agent in an amount of from about 35 to about 80% by weight, and a glidant in an amount of from about 5 to about 25% by weight, based on the weight of the coating composition.

In an especially preferred embodiment of the first aspect said coating composition comprises a film forming agent in an amount of about 20% by weight, an adhesion enhancing agent in an amount of about 60% by weight, and a glidant in an amount of about 20% by weight, based on the weight of the coating composition.

In another especially preferred embodiment of the first aspect said coating composition comprises a film forming agent in an amount of about 30% by weight, an adhesion enhancing agent in an amount of about 50% by weight, and a glidant in an amount of about 20% by weight, based on the weight of the coating composition.

In another especially preferred embodiment of the first aspect said coating composition comprises an adhesion enhancing agent in an amount of about 80% by weight, and a glidant in an amount of about 20% by weight, based on the weight of the coating composition.

Examples of said film forming agent suitable for incorporation into the coating composition of the first aspect of the present invention include cellulosephthalateacetate, microcrystalline cellulose, methylcellulose, hydroxypropyl methylcellulose, alginates, gum arabic, carboxymethylcellulose, hydroxyethylcellulose and methylcellulose.

Preferred film forming agents to be used according to the first aspect of the present invention are methylcellulose, hydroxypropyl methylcellulose, gum arabic, carboxymethylcellulose, hydroxyethylcellulose and methylcellulose, more preferable hydroxypropyl methylcellulose.

Examples of said adhesion enhancing agent suitable for incorporation into the coating composition of the first aspect of the present invention include dextrose, sorbitol, mannitol, sucrose, polyvinylpyrrolidone, lactose, starch, sodium starch glycolate, hydroxypropylcellulose, ethylcellulose and maltodextrines.

Preferred adhesion enhancing agents suitable for incorporation into the coating composition of the first aspect of the present invention are sucrose, polyvinylpyrrolidone, hydroxypropylcellulose, ethylcellulose and maltodextrines, more preferable hydroxypropylcellulose.

Examples of said glidant suitable for incorporation into the coating composition of the first aspect of the present invention include polyethylene glycol, polypropylene glycol, triethyl citrate, mono-, di- or triacetates of glycerol and 1,2-propyleneglycol.

A preferred glidant suitable for incorporation into the coating composition of the first aspect of the present invention is polyethylene glycol.

Usually, the coating composition according to the first aspect has a gel point of about 40° C. or more, i.e. close to the transition point.

The solid dosage form coated with a coating composition, of the second aspect of the present invention usually is a caplet or a tablet to be coated with the coating composition of the present invention.

According to a further aspect of the present invention, there is provided a method of preparing a coating composition comprising bringing into association a film forming agent in an amount of from 0 to about 85% by weight, an adhesion enhancing agent in an amount of from about 10 to about 90% by weight, and a glidant in an amount of from about 5 to about 50% by weight, based on the weight of the coating composition.

According to a further aspect of the present invention, there is provided a method of preparing solid dosage form which comprises coating a solid dosage form core with a coating composition comprising a film forming agent in an amount of from 0 to about 85% by weight, an adhesion enhancing agent in an amount of from about 10 to about 90% by weight and a glidant in an amount of from about 5 to about 50% by weight, based on the weight of the coating composition.

Usually, said solid dosage form is a caplet or a tablet, preferably a caplet.

In one embodiment of the forth aspect of the present invention thereafter one or more caplets coated with said coating composition, can be filled into at least one capsule part so as to obtain capsules.

The capsule shell in which the caplet is to be enclosed preferably comprises two shell halves, a body portion and a cap portion. Other capsule shells comprising more than two parts are also possible. In a preferred embodiment the capsule shells to be used may be those as described in EP-A-0 891 180.

Surprisingly, it has been found that caplets coated with the coating composition according to the present invention, show a superior adhesion to the capsule shell parts they have been filled in.

Especially, experimental results show that capsules filled with caplets coated with the coating composition according to the present invention, are tamper-proof in a way that the caplets show a superior adhesion to capsule shell parts and a better adhesive strength than capsules of the prior art such as described in EP-A-0 891 180. This is also demonstrated below in the experimental part of the present specification.

If it was tried to remove capsule shell parts from capsules prepared by using caplets coated according to the present invention, it was found that a very high percentage of shell parts will break and pulling apart capsule shells without deteriorating the capsule shells is not possible.

Thus, in a further aspect the present invention provides a use of a coating composition comprising a film forming agent in an amount of from 0 to about 85% by weight, an adhesion enhancing agent in an amount of from about 10 to about 90% by weight, and a glidant in an amount of from about 5 to about 50% by weight, based on the weight of the coating composition, for applying to a solid dosage form so as to improve adhesion of said solid dosage forms to capsule shells.

Furthermore, it has been found that feeding of caplets on a vibratory feed to be used in a capsule manufacturing process (typically the caplet feeding speed on a vibratory plate is in a range of from 1 to 7 cm/sec) is highly improved by using caplets coated with the coating composition claimed according to the present invention.

In a preferred embodiment of the process of preparing capsules by using caplets, in a further step caplets coated with the coating composition claimed according to the present invention are filled into capsule shell parts and then the combined capsule shell parts are treated by cold shrinking so as to obtain capsules.

As a preferred procedure the capsule manufacturing process described in EP-A-0 891 190 could be used.

To further illustrate the present invention, the following illustrative examples are presented, without limitation:

EXAMPLE 1

In a first example different coating compositions having a composition as shown in Table 1 below, were coated on Capsugel 707 Placebo caplet cores so as to obtain coated caplets. These coated caplets were subjected to a feeding on a vibratory feed (caplet feeding speed on vibratory plate: 1 to 7 cm/sec). The behaviour of these coated caplets was visually tested, and the results obtained were the following:

TABLE 1

| Mixture (ratio, parts by weight) | vibratory feed |
| --- | --- |
| HPMC/PVP 50/50 | good |
| HPMC/HPC 40/60 | good |
| HPC/PEG 80/20 | medium |
| HPMC/HPC/PEG 20/60/20 | medium |
| HPMC/HPC/PEG 30/50/20 | medium |
| HPMC/HPC/PEG 40/40/20 | very good |

Abbreviations used:
HPMC = hydroxypropyl methylcellulose
PVP = polyvinyl pyrrolidone
HPC = hydroxypropylcellulose
PEG = polyethylene glycol 6000

EXAMPLE 2

Adhesion Results after Stability Storage

In this example samples of Press-fit gelcaps made with a standard HPMC coating (sample 1) and made with a coating composition according to the present invention (sample 2) were manufactured according to a standard process.

| Sample 1 | | | | |
| --- | --- | --- | --- | --- |
| Cores | Capsugel 707 Placebo * | | | |
| Shells Body | White opaque | | | |
| Shells Cap | Green opaque | | | |
| 3 months | Defects | Gap | Appearance | Quantity |
| 40° C./75% RH | 0 | 0 | OK | 150 |

* coated with HPMC

| Sample 2 | | | | |
| --- | --- | --- | --- | --- |
| Cores | Capsugel 708 Placebo ** | | | |
| Shells Body | White opaque | | | |
| Shells Cap | Green opaque | | | |
| 3 months | Defects | Gap | Appearance | Quantity |
| 40° C./75% RH | 0 | 0 | OK | 150 |

** coated with a mix of HPMC/HPC/PEG (40/40/20)

Thereafter these samples were stored for 3 months under room conditions and at 40° C. 75% RH, and adhesion and disintegration were measured.

CONCLUSIONS adhesion is stable at room conditions for both samples
at 40° C./75% RH the adhesion drops for the samples made with HPMC whilst it remains stable for the sample made with the new coating mixture.
Disintegration is equivalent for all samples and conforms to specifications.

1. Adhesion Results:

|  |  | Pullapart (N) | Std | Nb of broken |
|---|---|---|---|---|
| Sample 1 |  |  |  |  |
| T = 24 h | RC | 22.5 | 2.5 | 0% |
| T = 6 days | RC | 22.7 | 4.1 | 0% |
| T = 6 weeks | RC | 21.1 | 2.9 | 0% |
| t = 2 months | RC | 21.4 | 3.3 | 0% |
| t = 3 months | RC | 22.6 | 4.2 | 0% |
| t = 3 months | 40° C./75% RH | 8.4 | 3.0 | 0% |
| Sample 2 |  |  |  |  |
| T = 24 h | RC | 29.13 | 5.0 | 80% |
| T = 6 days | RC | 30.1 | 4.2 | 100% |
| T = 6 weeks | RC | 33.2 | 4.8 | 90% |
| t = 2 months | RC | 32.0 | 5.2 | 74% |
| t = 3 months | RC | 28.5 | 3.1 | 100% |
| t = 3 months | 40° C./75% RH | 27.2 | 3.7 | 100% |

2. Disintegration Results:

|  |  | Disintegration time | STD |
|---|---|---|---|
| Sample 1 |  |  |  |
| T = 0 | RC | 4 min 38 s | 37 s |
| T = 3 months | 40° C./75% RH | 5 min 06 s | 19 s |
| Sample 2 |  |  |  |
| T = 0 | RC | 3 min 41 s | 29 s |
| T = 3 months | 40° C./75% RH | 3 min 49 s | 40 s |

The invention claimed is:

1. A tamper-proof capsule comprising at least one capsule shell part and coated at least one core caplet, said core being coated with a coating composition comprising hydroxypropylmethylcellulose (HPMC) in an amount ranging from about 20% to about 40% by weight, hydroxypropylcellulose (HPC) in an amount ranging from about 40% to about 60% by weight, and polyethylene glycol (PEG) in an amount of about 20% by weight, all based on the weight of the coating composition, wherein the HPMC and HPC are present in a total amount of about 80% by weight of the coating composition.

2. The tamper-proof capsule of claim 1, wherein the HPMC is present in an amount of about 20% and the HPC is present in an amount of about 60%.

3. The tamper-proof capsule of claim 1, wherein HPMC is present in an amount of about 30% and the HPC is present in an amount of about 50%.

4. The tamper-proof capsule of claim 1, wherein HPMC is present in an amount of about 40% and the HPC is present in an amount of about 40%.

* * * * *

UNITED STATES PATENT AND TRADEMARK OFFICE
CERTIFICATE OF CORRECTION

| | | |
|---|---|---|
| PATENT NO. | : 8,557,294 B2 | Page 1 of 1 |
| APPLICATION NO. | : 13/034928 | |
| DATED | : October 15, 2013 | |
| INVENTOR(S) | : Robert Anthony Scott et al. | |

It is certified that error appears in the above-identified patent and that said Letters Patent is hereby corrected as shown below:

IN THE CLAIMS:

Claim 1, col. 6, line 16, "and coated at least one core caplet" should read --and at least one coated core caplet--.

Signed and Sealed this

Seventeenth Day of December, 2013

Margaret A. Focarino
*Commissioner for Patents of the United States Patent and Trademark Office*